United States Patent [19]

Kolinsky et al.

[11] 4,260,541

[45] Apr. 7, 1981

[54] METHOD FOR PRODUCING INTERNALLY PLASTICIZED POLY(VINYL CHLORIDE)

[75] Inventors: Miloslav Kolinsky, Prague; Vendelin Macho, Novaky; Juraj Porubsky, Bratislava; Vladislav Kuska, Novaky; Jaroslav Manas; Stanislav Sykora, both of Gottwaldov; Rudolf Lukas, Prague, all of Czechoslovakia

[73] Assignee: Ceskoslovenska Akademie Ved, Prague, Czechoslovakia

[21] Appl. No.: 76,766

[22] Filed: Sep. 18, 1979

[51] Int. Cl.$^3$ .............................................. C08L 67/02
[52] U.S. Cl. .......................... 260/45.8 NT; 260/16; 260/17 A; 260/29.2 UA; 260/29.2 N; 260/29.2 E; 260/29.6 NR; 260/45.85 R; 525/11; 525/27; 525/167; 525/170
[58] Field of Search .................. 525/11, 167, 27, 170; 260/29.2 UA, 29.2 N, 29.2 E, 29.6 NR, 45.8 NT, 45.85 R, 16, 17 A

[56] References Cited

U.S. PATENT DOCUMENTS

| | | | |
|---|---|---|---|
| 2,773,049 | 12/1956 | Cowec | 525/11 |
| 3,111,500 | 11/1963 | Bartl et al. | 525/281 |

*Primary Examiner*—J. Ziegler

[57] ABSTRACT

The invention relates to the method for producing internally plasticized poly(vinyl chloride) suitable for the purposes of earth insulation and medical care. The production method according to the invention consists in the polymerization or copolymerization of vinyl chloride in an aqueous dispersion medium in the presence of up to 50 weight %, related to vinyl chloride, of a polymeric plasticizer prepared by polyesterification of dicarboxylic acids and diols. If desired, the polymerization can be carried out also in the presence of up to 12 weight % of alkyl esters of cyanuric acid and/or the copolymer of ethylene with vinyl acetate as the stabilizers of polymer-chain structure. The polymerization is carried out to the conversion of vinyl chloride 55 to 94% at temperature −20° to +80° C. in the presence of an emulsifier and the resulting polymer is isolated and worked up in the known way.

3 Claims, No Drawings

METHOD FOR PRODUCING INTERNALLY PLASTICIZED POLY(VINYL CHLORIDE)

The invention pertains to the method for producing internally plasticized poly(vinyl chloride), particularly suitable for the purpose of earth insulations, using the common polymerization equipment.

It is know that poly(vinyl chloride) cannot be processed in a pure form, but only with various auxiliary compounds added, as plasticizers, heat and light stabilizers, lubricants, pigments, fillers, and the like. These additives enable the processing and render the desired properties required for a final article. The addition of plasticizers provides the material with flexibility, workability, thermoplasticity, increases the internal mobility of macromolecules, etc. The applied plasticizers are low-volatile liquid or solid organic compounds, e.g. the high-boiling esters of phthalic, sebacic, adipic, and phosphoric acids.

It appears that poly(vinyl chloride) plasticized in this way turns hard and brittle and loses the weight after some time due to the loss of plasticizer. This loss may be caused by the volatility of plasticizer, unsuitable atmospheric conditions, extraction with water or other liquids which dissolve the plasticizer or react with it, or by the migration of plasticizer in the contact with other materials.

It is very difficult to preclude this deterioration process. Some improvement was achieved by the application of high-molecular weight compounds with the plasticizing effect, so called polymeric plasticizers, e.g. polyester plasticizers or plasticizing polymers or copolymers, as a styrene-acrylonitrile copolymer, polyisobutylene, poly(vinyl ethers), and the like.

The both cases represent the external plasticizing and the respective plasticizer and other auxiliary compounds have to be introduced into poly(vinyl chloride) in such way, that the resulting plasticized poly(vinyl chloride) is perfectly homogeneous. The plasticizer is mechanically worked into powdered poly(vinyl chloride). It is therefore very difficult and laborious to prepare the perfectly homogeneous blend and a relatively long mixing, gelation and exposure to a high processing temperature are necessary. In addition, the external plasticizing is not quite satisfactory because the plasticizer tends to migrate to the surface and is evaporated or extracted eventually.

Substantial improvement was attained by so called internal plasticizing when a plasticizer or a similar compound is incorporated by polymerization into the chain of poly(vinyl chloride) and became its part. If the low-molecular weight plasticizers are used for this purpose, the desired improvement does not occur because low-molecular weight compounds act as effective chain transfer agents in the polymerization giving rise to the low-molecular weight polymer—the oligomeric product with wrong rheological properties which is useless for practice.

Czechoslovak Patent No. 140,523 claims the manufacturing of internally plasticized poly(vinyl chloride) by block polymerization carried out up to the conversion of 35 to 55%. Low yields and the difficult removal of polymerization heat are the main disadvantage. This polymer is designated exclusively for application as a damping material for electroacoustic purposes.

They are also know copolymers of vinyl chloride with acrylates (U.S. Pat. No. 3,544,661), but they form heterogeneous resin mixtures which do not have the required processing properties. The aim is the production of internally plasticized poly(vinyl chloride) suitable for the preparation of stable flexible foils for earth insulations where the long service life 50 to 70 years is required. The material should not lose its original properties in time, should not liberate the plasticizing components, should not undergo degradation, destruction and other processes under the effect of soil humidity and of the respective corossive compounds in underground water, or changes by temperature in the region $-50°$ to $+50°$ C., and has to be well processable.

The method for producing internally plasticized poly(vinyl chloride) suitable above all for the purpose of earth insulations and medical care consists according to this invention in the polymerization and/or copolymerization of vinyl chloride which is carried out in an aqueous dispersion medium, preferably in emulsion and/or suspension, in the presence of the polyester polymeric plasticizer prepared by polyesterification of dicarboxylic acids having 4 to 16 carbon atoms, preferably 6 to 12 carbon atoms, in the molecule and diols having 2 to 8 carbon atoms in the molecule, advantageously ethylene glycol, diethylene glycol, and 1,4-butanediol, in the amount up to 50 wt.% related to vinyl chloride, and if desired, also in the presence of alkyl esters of cyanuric acid, preferably of diallyl cyanurate and/or triallyl cyanurate, and/or in the presence of the ethylene-vinyl acetate copolymer, which contains 10 to 50 wt.% advantageously 30 to 45 wt.%, of vinyl acetate incorporated into the copolymer, as the stabilizer of polymer-chain structure in the amount up to 12 wt.%, preferably up to 5 wt.%, to the conversion of vinyl chloride 55 to 94 %, advantageously 70 to 90%, at the temperature $-20°$ to $+80°$ C. and the pressure corresponding to the respective temperature, and in the isolation and processing of the resulting polymer in the known way.

Polyesters of adipic, sebacic, and phthalic acid and glycols containing 2 to 8 carbon atoms in the molecule, preferably ethylene glycol or butylene glycol individually or in mixtures, or in combinations with other compounds, e.g. diols, advantageously with 1,2-propanediol, 1,3-butanediol, and 1,4-butanediol, are advantageously employed as the compounds which are able to be incorporated into the chains of poly(vinyl chloride) formed or to be bonded to these chains. These compounds are advantageously added in the amount up to about 50 wt.%. The polymeric compound of the molecular weight ranging from 2500 to 7000 is preferably used. To improve the mechanical properties while keeping the sufficient elasticity, a certain small amount of such organic compound is added to the polymerization mixture which is also incorporated into the polymer and act in the system as a "stabilizer" of polymer structure. Organic compounds with functional groups able to react with poly(vinyl chloride) chains are advantageously used for this purpose, as diallyl or triallyl cyanurate, or various copolymers which can be grafted on chains, as e.g. the copolymer of ethylene with vinyl acetate, in the amount up to 12 wt.%, advantageously up to 3 wt.%.

On the one hand, the polymeric plasticizers are perfectly distributed in the suspension particles of polymer since the moment of their formation, on the other, they are bonded to the free radicals of macromolecular chains of poly(vinyl chloride) above all by combination with radicals easily formed in the macromolecules of polyester at the α-position to ester groups. At the same time, only one chemical bond between the poly(vinyl chloride) macromolecule and, for example, the polyester macromolecule is entirely sufficient.

To achieve the perfect dispersion of vinyl chloride, comonomers, modifiers, and polymeric plasticizers in the polymerization (or also grafting) medium, common dispersing agents are used, as cellulose ethers, particularly methylhydroxypropyl cellulose, hydroxyethyl cellulose, methyl cellulose, and the like, partially hydrolyzed poly(vinyl acetate) or poly(vinyl alcohol), partially esterified multifunctional alcohols, partially saponified fats, etc., and sometimes also the products of emulsifiers, as sodium dodecylsulfate, sodium salts of sulfonated alkanes, sulfosuccinazes, and others.

EXAMPLES 1 TO 8

A glass pressure reactor of volume 1 dm$^3$, which was equipped with a duplicating jacket, a horseshoe stirrer with revolution control, and a pressure gauge, was charged with the polymeric plasticizer. The type and amount of plasticizer calculated on the expected amount of formed polymer are given in Table I. Then, the aqueous phase was added which contained 10.2 cm$^3$ of the water solution of methylhydroxypropyl cellulose of concentration 2.5 wt.% as a dispergator, 1 cm$^3$ of sodium hydroxide solution of concentration 1 wt.% as a "buffer", and 390 cm$^3$ of distilled water. Dilauroyl peroxide (0.15 g) and diisopropyl peroxocarbonate Perkadox 16 (0.029 g) were further added.

The reactor was closed, flushed with a small amount of vinyl chloride to remove air and 100 g of vinyl chloride was let in under stirring (300 r.p.m.).

The content of reactor was rapidly heated to the polymerization temperature 51° C. rising the pressure to 0.74 MPa consequently. The polymerization was carried out at 51° C. under continuous stirring from 350 to 650 r.p.m. in such way, that the components were kept in suspension, as long as the pressure dropped from 0.74 MPa to 0.6 MPa. The total polymerization period ranged from 7.5 to 11 hours at this temperature, according to the amount and the type of polymeric plasticizer.

After the polymerization was finished, the content of reactor was rapidly cooled and the resulting product was threetimes decanted with warm distilled water, isolated by filtration, and dried at 25° C.

The examples 1 to 8 were carried out according to this procedure. Their results are shown in Table I.

EXAMPLES 9 TO 13

A stainless-steel autoclave of volume 8 dm$^3$, which was equipped with a duplicating jacket, a propeller agitator, breaking partitions at the inner wall of reactor, and a pressure gauge, was charged with the polymeric plasticizer. Its type and amount (calculated on the expected amount of resulting polymer) are given in Table I.

The aqueous phase was then added which consisted of 147.6 g of 2.5 wt.% water solution of methylhydroxypropyl cellulose as a dispersion agent, 6 dm$^3$ of 1.2 wt.% NaOH solution as a buffer agent, and 4000 g of distilled water.

Dilauroyl peroxide (2.2 g) and diisopropyl peroxocarbonate Perkadox 16 (0.3 g) were then added.

The reactor was flushed with a small amount of vinyl chloride to remove air, 1000 g of vinyl chloride was let in under stirring (150 r.p.m.), and the reactor was heated to 59.5° C. causing the pressure increase to 0.91 MPa.

TABLE I

| Example no. | Polymerization temperature (°C.) | Polymerization time (h) | Type of polymeric plasticizer (polyester) | Polymeric plasticizer Added (g) | Content in product (%) | Conversion (g) | Conversion (%) | K value |
|---|---|---|---|---|---|---|---|---|
| 1 | 51 | 8,00 | Adipic acid + ethylene glycol | 15 | 21,74 | 69 | 69 | 55,9 |
| 2 | 51 | 7,45 | | 20 | 27,39 | 73 | 73 | 52,6 |
| 3 | 51 | 8,00 | Adipic acid + 1,2-propanediol | 17,5 | 20,58 | 85 | 85 | 64,5 |
| 4 | 51 | 7,45 | | 23 | 25,84 | 89 | 89 | 61,3 |
| 5 | 51 | 11,00 | Adipic acid + 1,4-butanediol | 15 | 17,44 | 86 | 86 | 62,5 |
| 6 | 51 | 7,30 | | 20 | 22,22 | 90 | 90 | 60,1 |
| 7 | 51 | 8,00 | Sebacic acid + 1,4-butanediol | 15 | 22,72 | 66 | 66 | 58,7 |
| 8 | 51 | 8,30 | | 20 | 22,72 | 88 | 88 | 58,7 |
| 9 | 59,5 | 6,30 | Adipic acid + ethylene glycol | 152 | 16,6 | 895 | 72,0 | 51,6 |
| 10 | 59,5 | 6,15 | | 240 | 20,6 | 1165 | 79,5 | 53,1 |
| 11 | 59,5 | 4,00 | Adipic acid + 1,4-butanediol | 150 | 17,6 | 850 | 69,3 | 51,3 |
| 12 | 59,5 | 4,30 | | 240 | 21,2 | 1130 | 78,8 | 55,7 |
| 13 | 59,5 | 4,15 | Sebacic acid + 1,4-butanediol | 180 | 15,7 | 1143 | 79,3 | 58,0 |

The polymerization mixture was maintained at temperature 59.5° C. under stirring at 150 r.p.m. as long as the pressure decreased from 0.91 MPa to 0.7 MPa. The total polymerization period was 8 hours.

After the polymerization was completed, the content of the reactor was rapidly cooled and the resulting polymer was three-times decanted with warm distilled water, filtred, and dried at temperature 25° to 30° C.

The examples 9 to 13 were carried out according to this procedure and their results are in Table I. Some basic properties of the samples of internally plasticized poly(vinyl chloride) prepared in this way are given in Table IIa and IIb.

The following physico-chemical characteristics were determined with the samples of internally plasticized poly(vinyl chloride) prepared according to Examples 9 to 13:

TABLE IIa

| Characteristics | Unit | Sample according to Example no. | | | | |
| | | 9 | 10 | 11 | 12 | 13 |
|---|---|---|---|---|---|---|
| Bulk weight | g.dm$^{-3}$ | 611,9 | 662,8 | 586,2 | 600,0 | 577,7 |
| Screen analysis | | | | | | |
| 350 μm | % | 21,32 | 28,8 | 0,36 | 0,2 | 0,4 |
| 250 μm | % | 37,54 | 50,9 | 0,92 | 0,48 | 0,52 |
| 63 μm | % | 70,52 | 78,6 | 78,44 | 83,52 | 89,8 |
| Absorption of plasticizer | min | 5 | 7 | 4 | 4 | 4 |
| Thermal stabi- | | | | | | |

TABLE IIa-continued

| Characteristics | Unit | Sample according to Example no. | | | | |
|---|---|---|---|---|---|---|
| | | 9 | 10 | 11 | 12 | 13 |
| lity at 180° C. | min | 120 | 120 | 85 | 75 | 120 |

The samples of internally plasticized poly(vinyl chloride), which were prepared according to Examples 9 to 13, were further tested in two series:
(A) In blends without pigments
(B) In blends filled with carbon black Ad(A) The blends were prepared according to the following formula:

| | |
|---|---|
| Internally plasticized poly(vinyl chloride) (samples 9 to 13) | 200 wt. parts |
| Advastab BC 26 | 4 wt. parts |
| Dioctyl adipate | 40 wt. parts |
| Irgastab CH 300 | 1,5 wt. parts |
| Wax E | 1,5 wt. parts |
| Stearin | 0,5 wt. parts |

Each blend of the given composition was homogenized in a two-roll mill (350×600 mm) at temperature 162° to 165° C. for 8 min. The rails of thickness 0.6 mm were used for the determinations of thermal stability which is presented in Table IIb.

TABLE IIb

| Characteristics | Unit | Sample according to Example No. | | | | |
|---|---|---|---|---|---|---|
| | | 9 | 10 | 11 | 12 | 13 |
| Thermal stability at 180° C. | min | 120 | 120 | 85 | 75 | 120 |

Another part of the foils was repressed in a multistage press at 170° C. to foils of thickness 1 mm. These foils were used for measuring of physico-mechanical characteristics. The results are given in Table IIc.

TABLE IIc

| Characteristics | Unit | Sample according to Example no. | | | | |
|---|---|---|---|---|---|---|
| | | 9 | 10 | 11 | 12 | 13 |
| Tensile strength | MPa | 16,2 | 14,2 | 15,6 | 13,8 | 17,6 |
| Breaking elongation | % | 401 | 383 | 385 | 421 | 424 |
| Tear resistance | N/mm | 17,8 | 11,8 | 16,0 | 11,1 | 16,7 |
| Hardness Shore A | °Sh | 85 | 82 | 83 | 79 | 86 |
| Shore B | °Sh | 32 | 28 | 30 | 26 | 33 |
| Internal elec. resistivity | Ohm | — | — | — | — | — |

The tensile strength as well as the Shore hardness correspond to the content of incorporated polymeric plasticizer. Samples 9, 10 and 13 exhibit the substantially higher thermal stability than samples 11 and 12.

Ad(B) The second series of testing was carried out with blends filled with carbon black (8% Ketjenblack EC) where the content of dioctyl adipate was adepted with respect to the various content of grafted polymeric plasticizer.

The following results given in Table IId were obtained by measuring the characteristics of repressed foils:

TABLE IId

| Characteristics | Unit | Sample according to Example no. | | | | |
|---|---|---|---|---|---|---|
| | | 9 | 10 | 11 | 12 | 13 |
| Tensile strength | Mpa | 12,2 | 12,4 | 11,6 | 12,0 | 12,5 |
| Breaking elongation | % | 202 | 172 | 238 | 188 | 228 |
| Tear resistance | N/mm | 7,64 | 8,10 | 7,45 | 7,64 | 8,14 |
| Hardness Shore A | °Sh | 88 | 90 | 89 | 86 | 91 |
| Shore B | °Sh | 40 | 41 | 37 | 38 | 39 |
| Internal. elec. resistivity | Ohm | $1.10^4$ | $1.10^4$ | $3.10^4$ | $2.10^4$ | $4.10^4$ |

EXAMPLES 14 TO 17

The procedure was the same as in Examples 9 to 13 with the distinction that 1000 g of vinyl chloride was polymerized at 48° C. as long as the initial pressure 0.71 MPa decreased to 0.60 MPa. The results obtained in Examples 14 to 17 are shown in Table IIIa.

The samples of internally plasticized poly(vinyl chloride) according to Examples 16 and 17 were characterized by their physico-chemical properties both pigmented and without pigment.

The blends without pigments were prepared according to the formula used in Example 9 to 13. Also the foils for measuring the physico-chemical properties were prepared in the same way as in Examples 9 to 13.

TABLE III

| Example no. | Polymerization temperature (°C.) | Polymerization time (h) | Type of polymeric plastizier (polyester) | Polymeric plasticizer | | Conversion | | K value |
|---|---|---|---|---|---|---|---|---|
| | | | | Added (g) | Content in product (%) | (g) | (%) | |
| 14 | 48,0 | 8 | | 150 | 24,1 | 621 | 47,1 | 62,9 |
| 15 | 48,0 | 8 | Adipic acid + ethylene glycol | 200 | 29,7 | 715 | 51,5 | 60,9 |
| 16 | 48,0 | 8 | | 83 | 14,1 | 592 | 50,9 | 65,6 |
| 17 | 48,0 | 8 | | 117 | 18,9 | 617 | 50,0 | 64,6 |

About 11% of carbon black (Ketjenblack EC) was added into pigmented blends. The obtained results are presented in Table IIIb.

TABLE IIIb

| Characteristics | Unit | Sample according to Example no. | | | |
|---|---|---|---|---|---|
| | | Without pigments | | Pigmented | |
| | | 16 | 17 | 16 | 17 |
| Tensile strength | Mpa | 26,6 | 23,9 | 19,8 | 19,1 |
| Breaking elongation | % | 418 | 490 | 332 | 304 |
| Tear resistance | N/mm | 21,8 | 21,5 | 9,42 | 9,58 |
| Hardness Shore A | °Sh | 90 | 86 | 91 | 92 |
| Shore B | °Sh | 38 | 32 | 43 | 44 |
| Internal elec. resistivity | Ohm | — | — | — | — |
| Frost resistance NHSP | °C. | −31 | −30 | −11 | −6 |

EXAMPLES 18 TO 20

A 2 dm³ stainless-steel autoclave equipped with a duplicating jacket and a horseshoe stirrer (300 r.p.m.) was charged with 810 g of distilled water, 90 g of the 2 wt.% water solution of methylhydroxypropyl cellulose, 0.8 g of trichloroethylene, 0.04 g of sodium hydroxide, 1.4 g of dilauroyl peroxide, and 0.2 g of di(tert-butylcyclohexyl) peroxocarbonate. Polyesterpolyol prepared by polyesterification of adipic acid with ethylene glycol and 1,4-butanediol and having the following physicochemical properties: density at 20° C. 1.18 g.cm$^{-3}$, at 30° C. 1.16 g.cm$^{-3}$, and at 50° C. 1.15 g.cm$^{-3}$, dynamic viscosity at 20° C. 28.531 Pa.s (28931 cP), at 30° C. 13.018 Pa.s. (13018 cP) and at 50° C. 3.93 Pa.s (3930 cP), average molecular weight 3676, acid no. 1.6 mg KOH/g; hydroxyl no. 42.9 mg KOH/g; water content 0.035 wt.%, was then added under continuous stirring in the amount of 210 g.

Air was removed, 700 g of vinyl chloride was let in, and the temperature was raised to 56° C. The pressure in autoclave reached 1 MPa after attaining this temperature. The polymerization was carried out at the given temperature for 6 hours and the pressure dropped during this time to 0.6 MPa.

The content of autoclave was then rapidly cooled and quantitatively discharged. The suspension polymer was filtered, threetimes washed on filter with warm water, and dried at temperature 50° C.

The Examples 18 to 20 were carried out according to this procedure. The results are shown in Table IVa; some basic characteristics of the prepared samples of internally plasticized poly(vinyl chloride) are given in Tables IVb and IVc.

Some basic characteristics of the samples of internally plasticized poly(vinyl chloride) which were prepared according to the procedure described for Examples 18 to 20:

TABLE IVa

| Example no. | Polymerization temperature (°C.) | Polymerization time (h) | Type of polymeric plasticizer (polyester) | Polymeric plasticizer Added (g) | Polymeric plasticizer Content in product (%) | Conversion (g) | Conversion (%) | K value |
|---|---|---|---|---|---|---|---|---|
| 18 | 56 | 6 | Adipic acid + | 210 | 29,9 | 703 | 70,4 | 50,5 |
| 19 | 56 | 7 | ethylene glycol | 175 | 24,6 | 710 | 76,0 | 52,5 |
| 20 | 56 | 7 | Adipic acid + 1,4-butanediol | 150 | 21,2 | 709 | 79,8 | 53,8 |

10 g of powdered poly(vinyl chloride) of each sample 18 to 20 was extracted with 100 g of boiling methanol for 3 hours. The extracted amounts were:

| Sample 18 | 8.2 wt. % of polyesterpolyol polymeric plasticizer |
| Sample 19 | 7.4 wt. % of polyesterpolyol polymeric plasticizer |
| Sample 20 | 6.8 wt. % of polyesterpolyol polymeric plasticizer |

The following physicochemical properties given in Table IVb were determined with the samples of internally plasticized poly(vinyl chloride) prepared according to Example 18 to 20.

TABLE IVb

| Characteristics | Unit | Sample according to Example no. (unextracted) 18 | 19 | 20 |
|---|---|---|---|---|
| Bulk weight | g.dm$^{-3}$ | 654 | 731 | 610 |
| Screen analysis | | | | |
| 250 μm | % | 8,2 | 1,2 | 60,6 |
| 100 μm | % | 8,2 | 25,4 | 24,2 |
| 63 μm | % | 73,6 | 74,4 | 15,2 |
| Absorption of plasticizer | min | 3 | 10 | 4 |

Both unextracted and extracted samples of the suspension internally plasticized poly(vinyl chloride) were used for preparation of soft foils with 1.5 wt.% of basic lead stearate added as a heat stabilizer and 0.5 wt.% of wax as an external lubricant, by calendering at temperature 150° C. for 5 min. Table IVc shows the thermal stabilities of samples prepared according to Examples 18 to 20.

TABLE IVc

| Characteristics | Unit | Sample according to Example no. | | | | | |
|---|---|---|---|---|---|---|---|
| | | 18 | 18E | 19 | 19E | 20 | 20E |
| Thermal stability at 150° C. | min | 94 | 94 | 95 | 96 | 98 | 102 |

Note:
E means the sample extracted with methanol.

EXAMPLES 21 TO 24

A glass pressure reactor of volume 1 dm$^3$, which was equipped with a duplicating jacket, a horseshoe stirrer with revolution control, and a pressure gauge, was charged with the polymeric plasticizer and a crosslinking agent, the type and amount of which are given in Table V. Then the aqueous phase was added which contained 18 cm$^3$ of 2.5 wt.% water solution of methylhydroxypropyl cellulose as a dispersion agent, 1.9 cm$^3$ of 5.1 wt.% solution of sodium hydroxide as a "buffer" and 350 cm$^3$ of distilled water. Dilauryl peroxide (0.25 g) and diisopropyl peroxocarbonate (0.08 g) were further added.

The reactor was closed, flushed with a small amount of vinyl chloride to remove air, and 180 g of vinyl chloride was let in under stirring (300 r.p.m.).

The content of reactor was rapidly heated to the polymerization temperature 51° C. and the pressure increased to 0.76 MPa consequently. The polymerization was carried out at 51° C. under continuous stirring at 350 to 650 r.p.m., to keep the components in suspension, as long as the pressure dropped from 0.76 MPa to 0.61 MPa. The total polymerization time ranged from 6.5 to 8.5 h with respect to the amount and the type of added polymeric plasticizer and crosslinking agent.

After the polymerization was finished, the reactor content was rapidly cooled and the resulting product was threetimes decanted with warm distilled water, filtered, and dried at 25° C.

Examples 21 to 24 were carried out according to the above procedure and their results are shown in Table V.

Internally plasticized poly(vinyl chloride) prepared in this way is particularly suitable for manufacturing of earth-insulating flexible foils of long service life and for the purposes of medical care (bags for blood and infusion solutions, catheters, transfusion sets, and the like).

TABLE V

| Example no. | Polymerization temperature (°C.) | Polymerization time (h) | Polymeric stabilizer/Stabilizing agent | | | Conversion | | K value |
|---|---|---|---|---|---|---|---|---|
| | | | Components | Added (g/%) | Content in product (%) | (g) | (%) | |
| 21 | 51 | 8,0 | Adipic acid + 1,4-butanediol | 20/1 | 14,8/0,7 | 155 | 75,0 | 66,3 |
| 22 | 51 | 8,5 | Adipic acid + 1,4-butanediol + triallyl cyanurate | 30/1,5 | 23,4/1,2 | 158 | 71,2 | — |
| 23 | 51 | 6,5 | Adipic acid + 1,4-butanediol | 40/3 | 32/2,4 | 165 | 69,4 | 62,2 |
| 24 | 51 | 7,0 | Adipic acid + 1,4-butanediol + copolymer ethylene/vinyl acetate | 35/2 | 26,9/1,5 | 167 | 72,2 | 59,3 |

We claim:

1. A method for producing internally plasticized poly(vinylchloride) which is suitable primarily for the purposes of earth insulation and medical care, wherein vinyl chloride is polymerized in an aqueous dispersion medium in the presence of up to 50 weight % based on vinyl chloride of a polyester polymeric plasticizer, which is prepared by polyesterification of dicarboxylic acids selected from the group consisting of adipic and sebacic acid and diols having 2 to 8 carbon atoms in the molecule selected from the group comprising ethylene glycol, diethylene glycol, 1,2-propandiol and 1,4-butandiol in the presence up to 5 wt.% of a stabilizer of the polymer chain structure, to effect a 50–90% conversion of the vinyl chloride at temperatures from −20° to +80° C. and a pressure up to 1 MPa; and wherein the resulting polymer is isolated.

2. The method according to claim 1, wherein said stabilizer is triallylcyanurate.

3. The method according to claim 1, wherein said stabilizer is an ethylene-vinyl acetate copolymer containing from 30 to 45 wt.% of vinyl acetate.

* * * * *